United States Patent [19]

Rushatz et al.

[11] Patent Number: 4,979,732

[45] Date of Patent: Dec. 25, 1990

[54] EXERCISE AND REHABILITATIVE APPARATUS AND METHOD OF EXERCISING

[75] Inventors: Alfred S. Rushatz; James A. Peterson, both of West Point, N.Y.

[73] Assignee: Lifemates, Inc., Rosemont, Ill.

[21] Appl. No.: 384,444

[22] Filed: Jul. 25, 1989

[51] Int. Cl.[5] .................................................. A61F 5/04

[52] U.S. Cl. ........................................ 272/93; 272/903; 272/144

[58] Field of Search ................. 272/93, 116, 117, 118, 272/902, 903, 125, 126, 143, 144; 128/25 R; 434/247, 251

[56] References Cited

U.S. PATENT DOCUMENTS

| | | | |
|---|---|---|---|
| 1,904,039 | 4/1933 | Bruder . | |
| 2,046,653 | 7/1936 | Petcoff . | |
| 2,058,563 | 10/1936 | Campbell . | |
| 2,212,119 | 8/1940 | Julsrud et al. | 272/93 |
| 2,335,290 | 11/1943 | Medaris . | |
| 2,533,273 | 12/1950 | MacGregor . | |
| 2,703,080 | 3/1955 | Sanders . | |
| 3,117,782 | 1/1964 | Johnston . | |
| 3,721,434 | 3/1973 | Spies . | |
| 3,735,979 | 5/1973 | Levenberg . | |
| 3,779,540 | 12/1973 | Boudreau . | |
| 3,834,694 | 9/1974 | Pridgen . | |
| 3,921,975 | 11/1975 | Pridgen . | |
| 4,127,120 | 11/1978 | Applegate . | |
| 4,194,500 | 3/1980 | Grimaldi . | |
| 4,478,413 | 10/1984 | Siwula . | |
| 4,511,137 | 4/1985 | Jones . | |
| 4,519,106 | 5/1985 | Sandquist . | |
| 4,678,185 | 7/1987 | McIntyre et al. . | |
| 4,706,953 | 11/1987 | Graham . | |
| 4,819,936 | 4/1989 | Muller | 272/903 |
| 4,832,336 | 5/1989 | Lahman . | |

*Primary Examiner*—Richard J. Apley
*Assistant Examiner*—Lynne A. Reichard
*Attorney, Agent, or Firm*—Eric P. Schellin

[57] ABSTRACT

There is disclosed an exercise device and method of using same. The device consists of two hinged planar parts with a holding strap. A user assumes a prone face-up position on the device with the pelvic area being encompassed by the strap thereby stabilizing the torso of the user. An aide assists in both holding down the device and in assisting in alternatively raising the legs of the user thereby exercising groups of muscles.

3 Claims, 2 Drawing Sheets

EXERCISE AND REHABILITATIVE APPARATUS AND METHOD OF EXERCISING

FIELD OF THE INVENTION

The present invention relates to an apparatus and method for exercising and rehabilitating specific muscle groups, and more particularly to an apparatus for stabilizing the pelvis and isolating lumbar muscles during exercise, and to a method of exercise using the apparatus of the invention for stretching and strengthening hamstring, lower back and buttock muscles with the aid of a training partner.

BACKGROUND OF THE INVENTION

Exercise of specific muscle groups to improve and/or maintain muscular fitness has become fashionable today in the belief that the more effective functioning of the body leads to a more active and fulfilling life style and a more stable psyche. Exercise has therefore become the primary activity of numerous households, corporations, and public and private institutions today.

Typically, exercise can be "dynamic", i.e., including such activities as running or jogging, swimming, bicycling, tennis, basketball, football or skiing, or it can be "static", i.e., including such activities as weight lifting or isometrics.

Where caution is not taken to avoid overindulgence or overexertion before one's body has been properly conditioned, an undesirable, yet almost inescapable consequence, of exercise is injury to bodily tissues, as for example, muscles. Rehabilitative exercise is then necessary to strengthen the injured tissues, and to facilitate maintenance of those tissues newly strengthened.

Of course injury can and does occur on the job and may also involve individuals who let themselves deteriorate as far as muscular fitness is concerned. Their musculature atrophies, weaken and is subsequently injured (through stress/strain) and rehabilitation is necessary. Even fit individuals (athletes etc.) also injure themselves via over exertion during athletic contests, workouts, etc. and also require rehabilitative training.

OBJECTS AND SUMMARY OF THE INVENTION

The principal object of the present invention is to provide a unique apparatus designed for use by the person performing the rehabilitative exercise as well as provide a unique method for exercising specific muscle groups with the aid of an assistant while using the apparatus of the present invention.

Another object of the present invention is to provide a method of rehabilitating injured musculature which facilitates muscular stimulation through a regime of both stretching exercises as well as strengthening exercises.

Still another object of the present invention is to provide a special designed support board for the body of a person performing the stretching and strengthening exercises according to the method of the present invention.

All of the foregoing objects will be achieved by the provision of a support board according to the present invention which includes a pair of hinged supporting portions, the first of the supporting portions being a "back" supporting portion and the second of the supporting portions being the "pelvic" stabilizing portion. Both the back supporting and pelvic stabilizing portions include a padded area with the cushion member of the back supporting portion being uniquely configured to provide protection for any person's spinal column. A restraining strap is attached to one end region of the pelvic stabilizing portion adjacent the hinging elements securing the first and second portions together for encircling and securing the exercising and/or rehabilitating person's pelvic region to the support board, thereby immobilizing the pelvic region of the exercising person's body while the exercises of the present invention are being performed with the aid of the training partner.

The exercise of the present invention consist of first a stretching phase followed by a strengthening phase for strengthening the muscle groups concerned. Both the stretching and strengthening phases are performed by both the person whose muscles groups are being exercised as well as a therapist or training partner, the latter providing the stretching force as well as an "intelligent" resistance against which the person exercising exerts himself in order to properly carry out the routine of exercises prescribed for the strengthening portion of the exercise.

BRIEF DESCRIPTION OF THE DRAWINGS

These and other objects and advantages will become more apparent when considered in conjunction with the following detailed description of this invention and the drawings, in which.

The pelvic stabilizing portion also provides an area where the training partner places one of his feet in order to hold down the pelvic stabilizing portion of the apparatus, thereby immobilizing the exerciser's pelvic (hips), i.e., the hips are not permitted to come off the apparatus and the apparatus stays in contact with the floor. Without the restraining feature of the training partner's holding down the apparatus the board would move arcuately upward when the exerciser's legs are pushed back toward his head during the stretching portion of the exercise and/or when the exerciser trys to lower his legs against the training partner's applied resistance.

DETAILED DESCRIPTION OF THE PRESENT INVENTION

Figure 1:
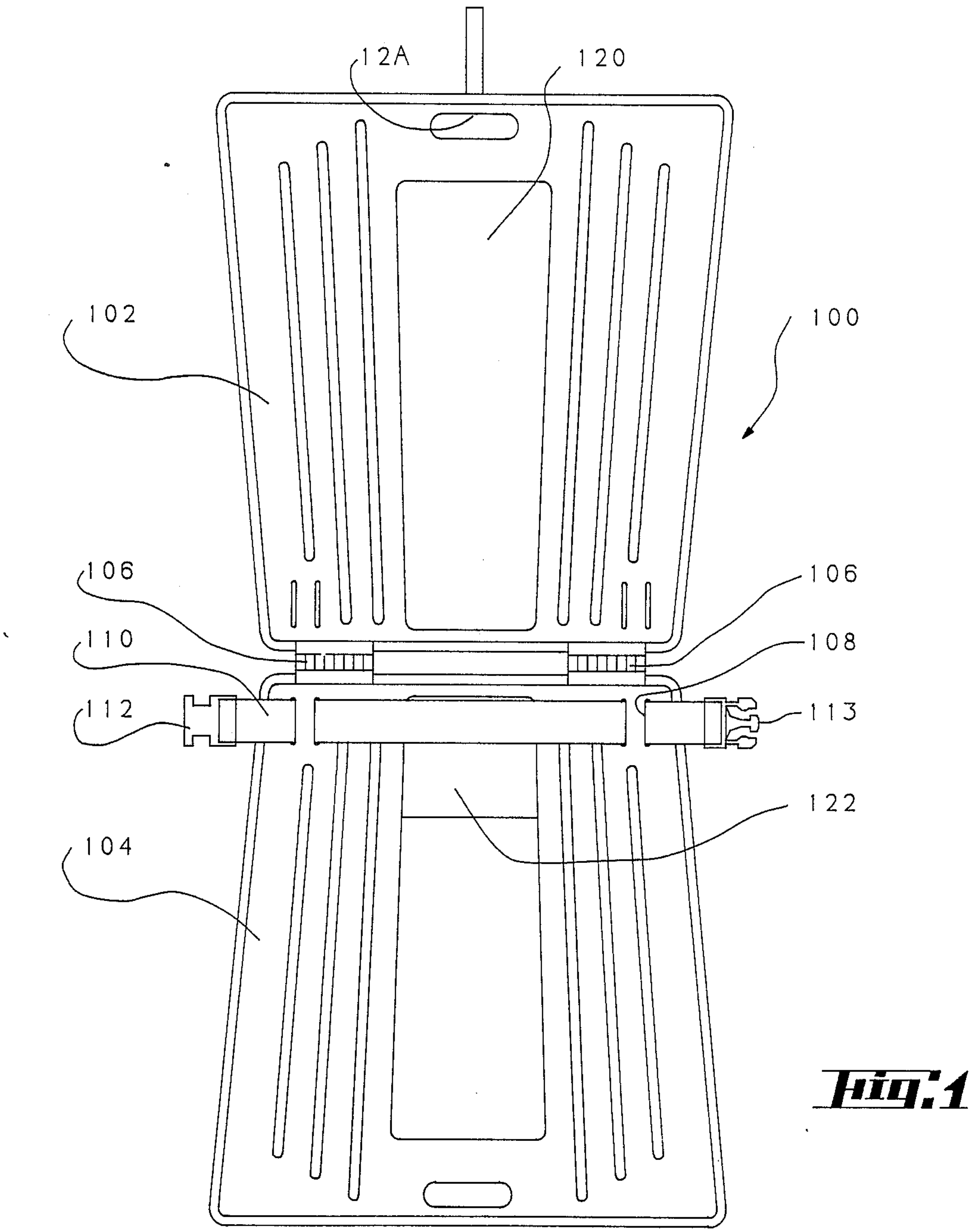
FIG. 1 illustrates the exercise support apparatus of the present invention in an open, ready-to-use position.

Referring now to FIG. 1 of the drawings, the exercise apparatus 100 of the present invention comprises a foldable support board having a first, upper body supporting portion 102 and a second, lower body supporting portion 104. The upper and lower body supporting portions are joined to one another by hinge elements 106, which may take the form of conventional leaf hinges disposed on opposite sides of the support board as shown in FIG. 1, or a single hinge element extending across the entire span of the mating edges of the two body supporting portions. The hinge means may also comprise a living hinge formed from an appropriate plastic material. Disposed on opposite sides of the lower body supporting portion 104 in close proximity to the hinge elements is a strap securing member which is a continuous strap which is threaded through slots in portion 104, 108. The strap 110, has the female portion 112 at one end, and the male portion of the quick-release fastener at the other end, 113.

Padded members 120, 122 are provided in the upper and lower body supporting portions, respectively. Cushion member 120 is formed with a centrally located spinal protecting portion having a unique configuration. As shown in FIG. 1, the spinal protecting portion has a substantially inverted triangular configuration in which the width at the hinged edge region is narrower than the width at the edge region opposite the hinged edge region (i.e., the "free end region"), and has a height appropriately chosen to reach upwardly and protect the spinal column of the person using the exercise apparatus. By means of this unique configuration, all kinds of "backs" will be accommodated. In other words, the spinal curvature of the persons for whom the use of the support board of the present invention is contemplated may vary in configuration to include a wide range of shoulder-to-waist dimensions.

When the support board portions are folded one on top of the other, a latch (not shown) such as a Velcro strap may be used to secure the two portions together whereby the so secured portions assume the configuration of a closed briefcase.

Referring now to FIGS. 2–5, the method of using the exercise apparatus to perform the unique method of the present invention will now be explained.

Figure 2:
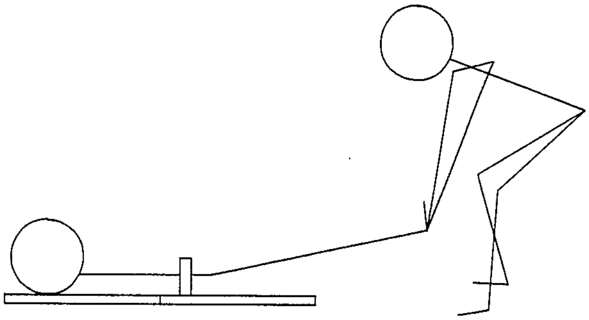
FIGS. 2-5 illustrate the manner in which the exercise support apparatus of the present invention is to be used in performing the novel method of this invention.

First, as shown in FIG. 2, the person who will be performing the exercises (the "subject") lies on his back on the support board 100, with his upper back positioned on the upper body supporting portion 102 and his buttocks and upper leg regions positioned over the lower body supporting portion 104. The restraining strap 110 is disposed about the subjects pelvic region and buckled securely in place snugly across the subject's hips.

Figure 3:
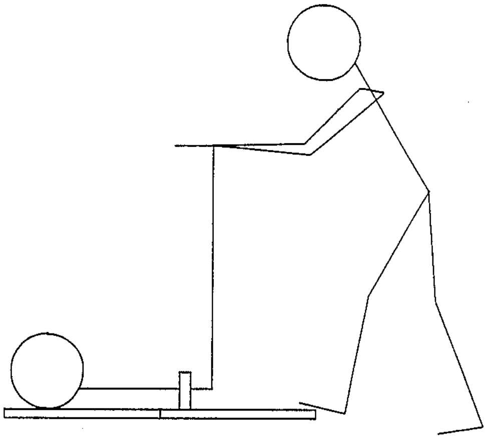
Figure 4:
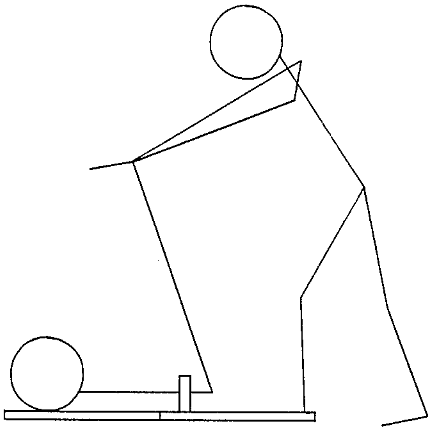

Next, the therapist or training partner (the "TP") positions himself as shown in FIG. 3 at the end of the support board 100 furthest from the subject's head. The assistant must stand with one foot on the non-hinged, free end of the lower body supporting portion 104 in order to hold down that end of the support board which, in turn, holds down the hips of the exerciser. The assistant then grasps each of the subject's legs at the ankles and, with the subject's knees locked, raises the legs to a location (see FIG. 4) where the legs form a 90° angle with the floor, or as close to 90° as possible. Since the restraining strap is securely buckled about the subject's pelvic region and the lower body portion of the support board is held on the ground by the assistant's foot, upon commencement of the exercise contemplated by the present invention, the subject's hips are prevented from being raised up off the board, and thus the muscles which contribute to lower back pain (the back extensor muscles) are more effectively exercised.

Once the subject and the assistant have assumed this position, the exercise routine takes on two phases: a first back, hamstring and buttocks stretching phase, and a second strengthening phase for these muscles.

Figure 5:
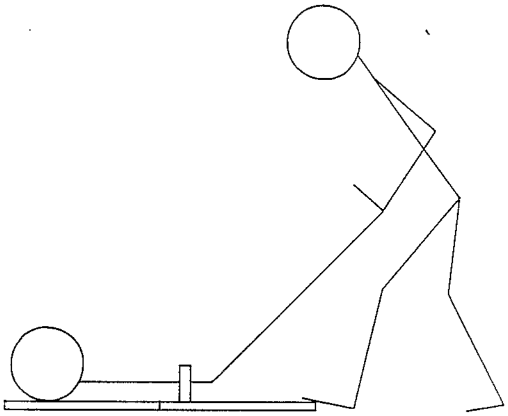

In the first phase, stretching of the lower back, buttocks and hamstring muscles of the subject is accomplished, as shown in FIG. 5, by forcing the legs of the subject toward his head and then moved back to the starting position. This movement is performed repetitively by the assistant to subject's lower back and leg muscles, with the TP urging the subject's legs a little further toward the subject's head with each repetitive cycle.

In the second phase, strengthening of the back, and buttocks muscles is accomplished by the subject lowering his legs against a resistance force provided by the TP (see FIG. 6). In other words, the assistant maintains the same grip on the ankles of the subject and resists the downward movement of the subject's legs so that the subject's legs are allowed to move only in a smooth, steady pattern down to a position where the legs are 45° to the floor. When the exerciser's legs have reached a position where they are 45° to the floor or lower position of the board the exerciser will be told to "STOP" and the TP will again raise the exerciser's legs to the 90° starting position so that the exercise can be performed once again. As in the first phase, the exercises in this phase should also be performed repetitively, for ten repetitions.

At all times during the stretching and strengthening phases of the exercise, the exerciser should keep his knees locked. In so doing, maximum stretching for both the hamstring and the lower back muscles during the first phase, and maximum strengthening of the lower back and buttock muscles during the second phase will be facilitated.

In performing the method of the present invention, it is important that the pelvic region of the subject be as immobilized as much as possible. This is accomplished by encircling the strap 110 of the board 100 about the hips of the exerciser, and then securely fastening the strap ends with the buckle (112 and 113) and the TP standing on the lower portion of the board during all phases of the regimen, i.e. stretching and strengthening.

Unlike conventional exercises for the back, the use of the restraining strap while the TP stands on the lower portion of the board, while using the board of the present invention provides utmost stabilization of the subject's pelvis and optimum isolation of the subject's lumbar muscles during the exercises. In addition, by lying flat on the surface of the board, the subject further reduces unwanted motion during both the rehabilitative exercise phases of the method. The high level of stabilization of the subject's pelvic region permits a more focused stretch of his lumbar (back extensor) muscles as well as his buttocks and hamstring muscles. In turn, this produces a gapping of the posterior structures (i.e., facets, soft tissue, etc.) in the lumbar region which reduces the pressure on the spinal nerve endings and leads to a corresponding decrease in back pain. Moreover, the stretching phase of the exercise also appears to stimulate the local mechanoreceptors to produce localized secretions of endorphins and enkephalins which further aid in pain reduction.

Performing the stretching portion of the exercise method of the present invention also appears to produce vigorous contraction of the hamstring and the lumber spine muscles. Such contraction allows each of these muscle groups to relax reflexively thereby permitting a greater range of motion in the back and lower extremities. The increased level of mobility and flexibility enables a greater range of movements without the typical mechanical lower back discomfort.

Performing the method of the present invention provides the subject with several additional advantages which collectively reduce the level of back pain during rehabilitation. For example, the isolated contractions of the lumbar muscles which occur during both the stretching and the strengthening phases stimulate an increase in local circulation in the lower back region, and the removal of some of the toxic metabolites which have accumulated in these muscles from lack of use. More importantly, however, strengthening of the postural muscles in one's lower back enables these muscles to sustain themselves longer without the buildup of toxic metabolites brought on by chronic fatigue. Stronger lower back muscles are better capable of permitting a subject to maintain proper body alignment, and are also less susceptible to being injured and more capable of withstanding the debilitating effects of outside forces on the body.

The foregoing is a description of the preferred embodiment of the present invention. However, it is to be understood that the embodiment so described is for purposes of example only and is not intended to limit the invention in any manner. It is further understood that modifications in the apparatus and method of the present invention evidencing a reasonable range of equivalents are contemplated.

What is claimed is:

1. A method of exercising the lower back muscles of a subject, with the aid of an assistant, comprising:

(a) causing the subject to lie on his back in a prone position on a support board, (b) securing the subject's pelvic region to the support board, (c) raising the legs of the subject to a first position in which the subject's legs are disposed at about a 90° angle to the floor, (d) pushing the subject's legs from said first position to a second position in which the subject's legs been moved toward his head, (e) repeating steps (c) and (d) a predetermined number of times, (f) allowing the legs of said subject to move from said first position to a third position in which the subject's legs are disposed at about a 45° angle to the floor, while the assistant provides a resistance to movement of the subject's legs from said first position to said third position, (g) repeating step (f) a predetermined number of times, whereby when step (d) is performed, the subject's hamstring and lumber back muscles are caused to be stretched, and when step (g) is thereafter performed, the subject's lower back and buttock muscles are strengthened.

2. The method of claim 1, wherein steps (d)-(g) are performed by said subject with the aid of said assistant.

3. The method of claim 1, wherein steps (c)-(g) are performed by said subject with the aid of said assistant.

* * * * *